(12) United States Patent
Ihm et al.

(10) Patent No.: US 9,329,165 B2
(45) Date of Patent: May 3, 2016

(54) CENTRIFUGAL SEPARATION KIT AND METHODS FOR CENTRIFUGAL SEPARATION USING THE SAME

(75) Inventors: Khi-Pyo Ihm, Seoul (KR); Hong Kim, Chungcheongnam-do (KR)

(73) Assignee: GLOTECH CO., LTD., Chungcheongnam-do (KR)

( * ) Notice: Subject to any disclaimer, the term of this patent is extended or adjusted under 35 U.S.C. 154(b) by 1048 days.

(21) Appl. No.: 13/318,810

(22) PCT Filed: Oct. 12, 2010

(86) PCT No.: PCT/KR2010/006973
§ 371 (c)(1),
(2), (4) Date: Nov. 4, 2011

(87) PCT Pub. No.: WO2011/052910
PCT Pub. Date: May 5, 2011

(65) Prior Publication Data
US 2012/0053041 A1   Mar. 1, 2012

(30) Foreign Application Priority Data

Oct. 28, 2009   (KR) .................. 10-2009-0102762

(51) Int. Cl.
*B01L 3/00*   (2006.01)
*G01N 33/49*   (2006.01)

(52) U.S. Cl.
CPC ............ *G01N 33/491* (2013.01); *B01L 3/5021* (2013.01); *B01L 3/50215* (2013.01); *B01L 2200/026* (2013.01); *B01L 2200/028* (2013.01); *B01L 2300/028* (2013.01); *B01L 2400/0409* (2013.01); *B01L 2400/0478* (2013.01)

(58) Field of Classification Search
CPC ............. B01L 3/5021; B01L 3/50215; B01L 2200/026; B01L 2200/028; B01L 2300/028; B01L 2300/047; B01L 2400/0409; B01L 2400/0478; G01N 33/491
See application file for complete search history.

(56) References Cited

U.S. PATENT DOCUMENTS

| | | | |
|---|---|---|---|
| 4,055,501 A * | 10/1977 | Cornell | ...................... 422/533 |
| 4,469,151 A | 9/1984 | Wilson et al. | |
| 4,824,560 A | 4/1989 | Alspector | |
| 4,950,745 A | 8/1990 | Ishido et al. | |
| 5,577,513 A | 11/1996 | Van Vlasselaer | |
| 2003/0205538 A1 | 11/2003 | Dorian et al. | |

(Continued)

FOREIGN PATENT DOCUMENTS

| | | |
|---|---|---|
| JP | 1991-167471 | 7/1991 |
| JP | 2000-189406 | 7/2000 |

(Continued)

OTHER PUBLICATIONS

International Application No. PCT/KR2010/006973; International Search Report issued Jun. 7, 2011 (3 pages).

*Primary Examiner* — Timothy Cleveland
(74) *Attorney, Agent, or Firm* — Meunier Carlin & Curfman LLC

(57) ABSTRACT

A centrifugal separation kit is used for centrifugally separating whole blood and body fluid, and a method for centrifugal separation using the kit. The centrifugal separation kit is capable of easily extracting a target substance by installing an injector to a centrifugal separation tube and collecting the centrifugally separated target substance with the injector.

7 Claims, 19 Drawing Sheets

(56) References Cited

U.S. PATENT DOCUMENTS

| | | | |
|---|---|---|---|
| 2005/0124073 A1* | 6/2005 | Freund | 494/43 |
| 2010/0025342 A1 | 2/2010 | Morimoto et al. | |
| 2010/0120596 A1 | 5/2010 | Froman et al. | |
| 2010/0140182 A1* | 6/2010 | Chapman et al. | 210/741 |

FOREIGN PATENT DOCUMENTS

| | | |
|---|---|---|
| JP | 2000-199760 | 7/2000 |
| JP | 2006-502388 | 1/2006 |
| JP | 2007-000536 | 1/2007 |

* cited by examiner

CENTRIFUGAL SEPARATION KIT AND METHODS FOR CENTRIFUGAL SEPARATION USING THE SAME

CROSS-REFERENCE TO RELATED APPLICATION

This application claims priority under 35 USC 119(a) to Korean Patent Application No. 10-2009-0102762 filed in the Republic of Korea on Oct. 28, 2009, the entire contents of which are incorporated herein by reference.

TECHNICAL FIELD

The present invention relates to a centrifugal separation kit used for centrifugally separating blood and body fluid, and a method for centrifugal separation using the same. More particularly, the present invention relates to a centrifugal separation kit capable of easily extracting a target substance by installing an injector to a centrifugal separation tube and collecting the centrifugally separated target substance with the injector, and a method for centrifugal separation using the same.

BACKGROUND ART

Along with the development of medical technologies, beneficial components present in body tissues such as stem cells or platelets are used for treating diseases or applied in surgical procedures.

The stem cells are classified into embryonic stem cells and adult stem cells as well known in the art, and the adult stem cells are known as being distributed in bone marrow, cord blood, or fat tissues.

Such a stem cell is defined as a cell having self renewal properties by which the cell is repeatedly divided, multipotency properties by which the cell is divided into various tissues, and pluripotency properties by which the cell is divided into all kinds of cells.

In addition, when a wound occurs, the platelet secretes growth factors through a series of cascade processes while trying to stop the bleeding. In more detail, the platelet is a Platelet Rich Plasma (PRP) included in the whole blood, which may be obtained by centrifugally separating the whole blood. The PRP includes Platelet-Derived Growth Factor (PDGF), Transforming Growth Factor (TGF), Epidermal Growth Factor (EGF), and so on. These growth factors are known as factors involved in controlling neovascular promotion essential to regeneration of tissues, chemotactic and maturation promotion of cells, stimulus and increase of stem cells, organic synthesis, and so on.

For this reason, the tendency to clinically utilize the stem cells and the Platelet Rich Plasma (PRP) is increasing.

Presently, various methods are being performed to extract a target cell from the stem cells or to efficiently obtain a platelet or a PRP from the whole blood.

When clinically extracting a target cell (an adult stem cell), the target cell is extracted from fat tissues and bone marrow, and the process of extracting the stem cell from the bone marrow is substantially similar to the process of extracting Platelet Rich Plasma (PRP) from the whole blood. For this reason, the process of extracting PRP from the whole blood will be described below.

First, an injector for collecting blood and a centrifugal separation tube for centrifugal separation are prepared. At this time, the injector uses a cylinder equipped with an injection needle and a common injector made to function like a piston, and the centrifugal separation tube is a common container which receives a predetermined substance therein and has an upper portion sealed by a cap.

The blood collecting injector is used for collecting the whole blood. Here, the injector employs a 10 cc blood-collecting injector. For example, 8.5 cc of blood is collected by using a 10 cc injector containing 1.5 cc of Acid Citrat Dextrose (ACD) solutions which is an anticoagulant, then put into a 10 cc centrifugal separation tube, and then centrifugally separated in a centrifugal separator.

If the blood is centrifugally separated, as shown in FIG. 1, the blood is divided into three layers of a Red Blood Cell (RBC) layer, a Platelet Rich Plasma (PRP) layer containing a lot of platelets, a Platelet Poor Plasma (PPP) layer from the bottom of a centrifugal separation tube 2 due to the specific weights. At this time, the Platelet Rich Plasma (PRP) is also called a buffy coat. In other words, the blood is divided into a blood cell component including the RBC layer and a blood cell plasma component including the Platelet Rich Plasma (PRP) and the PPP. At this time, Platelet Rich Plasma (PRP) is collected from the middle layer (PRP layer) other than the RBC layer and the PPP layer, by using a new 5 cc injector to which a long spinel needle is mounted.

Meanwhile, for the enrichment of platelets, the centrifugal separation process and the process of collecting the enriched Platelet Rich Plasma (PRP) are repeated again.

In this process, it is needed to give attention to not collecting the Red Blood Cell (RBC) together when the Platelet Rich Plasma (PRP) is collected. In other words, it is important to collect only the Platelet Rich Plasma (PRP) (blood plasma component). For this reason, in order to separate the Platelet Rich Plasma (PRP) layer and the RBC layer, a method for centrifugal separation by putting a cell isolation gel is used.

The cell isolation gel is an isolation solution with a concentration between the specific weight of the red blood cell and the specific weight of the platelet, and Ficoll™, Percoll™ or sucrose derivatives are used. In other words, as shown in FIG. 2, if blood is put into a centrifugal separation tube 2 including a cell isolation gel Vf and is treated by a centrifugal separator (not shown), the blood in the tube 2 is divided into an upper blood plasma component and a lower blood cell component with the cell isolation gel Vf as a border layer.

Therefore, as the RBC and the Platelet Rich Plasma (PRP) are separated by the cell isolation gel Vf, it is possible to safely collect only the Platelet Rich Plasma (PRP) by using a new 5 cc injector 1 to which a long spinel needle is mounted, so that the RCB is not extracted together from the Platelet Rich Plasma (PRP) layer (see FIG. 3).

As described above, various kinds of centrifugal separation tubes and injectors for extracting Platelet Rich Plasma (PRP) from the whole blood have been suggested. For example, Korean Patent Registration No. 10-0430893 discloses a serum dividing injector configured to collect blood by using an injector and then use the injector as a centrifugal separation tube, and Korean Utility Model Registration No. 20-0269465 discloses a centrifugal separation tube and a blood collecting injector containing a serum dividing gel, which forms a gel container in a blood collecting tube, collects blood therein, followed by cutting a container rod, and is sealed by a sealing cap and performs centrifugal separation.

However, the above methods consume too much time and collect the platelet layer (cell plasma components) inconsistently, and have the risk of red blood cell layers collecting together. Therefore, it is not easy to give accuracy to clinic applications. In addition, the consumption ratio of injectors and centrifugal separation tubes used for collecting the whole blood and extracting blood plasma components increases.

To solve this problem, an automatic classification technique, a Platelet Rich Plasma (PRP) separation kit, and a cell isolation gel have been developed.

However, the automated equipment for automatic classification may not be easily used at general private hospitals, when considering its price and efficiency.

In addition, though various kits of various prices and performances are provided suitably for individual private hospitals, there is a burden in using these kits due to their high prices and the increase of consumables.

Moreover, since Platelet Rich Plasma (PRP) necessary at a surgical procedure needs to be extracted and then instantly used, the waiting time increases when the Platelet Rich Plasma (PRP) is extracted, which deteriorates the working efficiency.

DISCLOSURE

Technical Problem

The present invention is designed to solve the problems of the prior art, and therefore it is an object of the present disclosure to provide a centrifugal separation kit capable of extracting a target substance by centrifugal separation in a convenient and stable way, and a method for centrifugal separation using the same.

Another object of the present disclosure is to provide a centrifugal separation kit capable of allowing cheap consumables to be used, decreasing the amount of consumables used, and improving the working efficiency by reducing the waiting time of a person who performs or receives a surgery, and a method for centrifugal separation using the same.

Technical Solution

In one aspect, there is provided a centrifugal separation kit installed to a centrifugal separator to divide a whole blood into blood cell components composed of a Red Blood Cell (RBC) layer and blood plasma components composed of a Platelet Rich Plasma (PRP) layer and a PPP (Platelet Pure Plasma) layer in order from the bottom, wherein the centrifugal separation kit includes: a centrifugal separation tube having a closed lower portion and an open upper portion and a cap for opening or closing the upper portion, the centrifugal separation tube including a collecting unit installed therein and having a collecting tube, the centrifugal separation tube being filled with a predetermined amount of cell isolation gel, and wherein the collecting unit is installed so that a space corresponding to the sum of volumes of the Red Blood Cell (RBC) of the centrifugally separated whole blood and the cell isolation gel is formed in a lower portion thereof.

In another aspect, there is also provided a centrifugal separation kit installed to a centrifugal separator to divide a whole blood into blood cell components composed of a Red Blood Cell (RBC) layer and blood plasma components composed of a Platelet Rich Plasma (PRP) layer and a PPP (Platelet Pure Plasma) layer in order from the bottom, the centrifugal separation kit includes: a centrifugal separation tube including a collecting unit installed therein and having a collecting tube, the centrifugal separation tube having a coupling unit installed to a lower portion thereof and having a tube insert portion communicating with the inside thereof, the centrifugal separation tube having an open upper portion; and a lower cap installed to the coupling unit of the centrifugal separation tube and filled with a predetermined amount of cell isolation gel, the lower cap having a fastening unit protruding upwards to seal the tube insert portion, wherein the collecting unit is installed so that a space corresponding to the sum of volumes of the Red Blood Cell (RBC) of the centrifugally separated whole blood and the cell isolation gel is formed in a lower portion thereof.

Preferably, the centrifugal separation kit further includes an injector having an opening at an upper portion thereof so that a piston having a rubber packing installed thereto is movably inserted into the open upper portion, the injector having an insert portion at a lower portion thereof to which an injector needle is installed thereto so that the whole blood is collected therein.

Preferably, an injector from which a piston and an injector needle are removed so that the rubber packing is present at the injector is inserted into the centrifugal separation tube having the open upper portion and installed to an upper portion of the collecting unit to be loaded on a centrifugal separator.

Preferably, the centrifugal separation tube has an inner diameter greater than an outer diameter of the injector, and an outer circumference of the injector is closely adhered to an inner circumference of the centrifugal separation tube.

Preferably, an upper portion of the collecting unit is shaped corresponding to a contact surface of the injector so that the insert portion of the injector is inserted into and closely adhered to the collecting tube.

Preferably, the collecting unit has a length greater than a length of the injector insert portion.

Preferably, in order for the blood plasma components obtained by separating the whole blood by the centrifugal separator to collect based on the collecting unit, a volumetric capacity (A) of the space in the lower portion of the collecting unit where the blood plasma components are generated, a whole blood Wb collected from the injector, a volume of the Red Blood Cell (RBC), a volume ratio (a) of the centrifugally separated Red Blood Cell (RBC), and a volume Vf of the cell isolation gel should satisfy the following relation:

$$A = (\alpha \times Wb) + Vf = Vb + Vf; \text{ and}$$

$$0 \leq Vf \leq Wb$$

Preferably, a ventilation hole is formed in the collecting unit so that the air in the centrifugal separation tube discharges out when a whole blood flows into the centrifugal separation tube, and the ventilation hole is closed as the injector is installed and closely adhered to the collecting unit.

Preferably, inclined protrusions are formed at regular intervals on an inner side of the centrifugal separation tube along a length direction of the centrifugal separation tube, and the collecting unit moves downwards as much as the interval of the protrusions due to a pressing force applied from the injector so as not to move upwards.

Preferably, the centrifugal separation tube is made of transparent material, and gradations representing a volume of the space located in the interval of the protrusions are marked on an outer circumference of the centrifugal separation tube so that the location of the collecting unit is adjusted according to the sum of a volume of the Red Blood Cell (RBC) in the collected whole blood and a volume of the filled cell isolation gel.

Preferably, the lower cap is closely adhered to a lower portion of the centrifugal separation tube, and a height of a location where the blood plasma component is generated is adjusted according to the degree of coupling.

Preferably, the lower cap is configured to be installed to the injector while sealing the insert portion of the injector.

In another aspect, there is also provided a method for centrifugal separation using the above centrifugal separation kit, which includes: (a1) preparing a centrifugal separation tube and an injector; (b1) collecting a whole blood by using the injector; (c1) installing the injector collecting the whole blood to the centrifugal separation tube; (d1) loading on the centrifugal separator the centrifugal separation tube to which the injector is installed; and (e1) operating the centrifugal separator to collect blood plasma components to the injector.

Preferably, in the step (c1), a piston and an injector needle are removed from the injector collecting the whole blood so that a rubber packing is present in the injector, and the injector is inserted in the centrifugal separation tube from which the cap is removed and is placed on the collecting unit.

Preferably, inclined protrusions are formed at regular intervals on an inner side of the centrifugal separation tube along a length direction of the centrifugal separation tube, and the collecting unit moves downwards as much as the interval of the protrusions due to a pressing force applied from the injector so as not to move upwards.

Preferably, gradations representing a volume of the space located in the interval of the protrusions are marked on an outer circumference of the centrifugal separation tube, and before the step (a1) or (b1), the location of the collecting unit is adjusted according to the sum of a volume of the Red Blood Cell (RBC) in the collected whole blood and a volume of the filled cell isolation gel so that blood plasma components are collected in the injector.

In another aspect, there is also provided a method for centrifugal separation using another centrifugal separation kit, which includes: (a2) preparing a centrifugal separation tube and an injector; (b2) collecting a whole blood by using the injector; (c2) installing a lower cap to a lower side of the centrifugal separation tube; (d2) installing the injector collecting the whole blood to the centrifugal separation tube; (e2) loading on a centrifugal separator the centrifugal separation tube to which the injector is installed; and (f2) operating the centrifugal separator to collect blood plasma components in the injector.

Preferably, in the step (d2), a piston and an injector needle are removed from the injector collecting the whole blood so that a rubber packing is present in the injector, and the injector is inserted into the centrifugal separation tube from which the cap is removed and is placed on the collecting unit.

Preferably, an upper portion of the collecting unit is shaped corresponding to a contact surface of the injector so that the insert portion of the injector is inserted into and closely adhered to the collecting tube.

Preferably, the centrifugal separation tube has an inner diameter greater than an outer diameter of the injector, and an outer circumference of the injector is closely adhered to an inner circumference of the centrifugal separation tube.

Preferably, the collecting unit has a length greater than a length of the injector insert portion.

DESCRIPTION OF DRAWINGS

Other objects and aspects of the present invention will become apparent from the following descriptions of the embodiments with reference to the accompanying drawings in which.

BEST MODE

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 1:
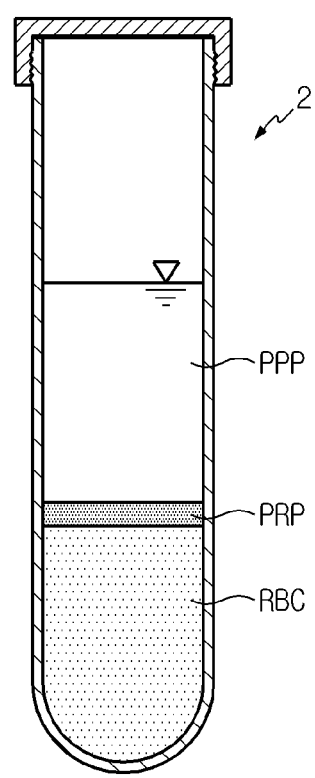
FIG. 1 is a cross-sectional view showing that a whole blood is centrifugally separated to a conventional centrifugal separation tube.
Figure 2:
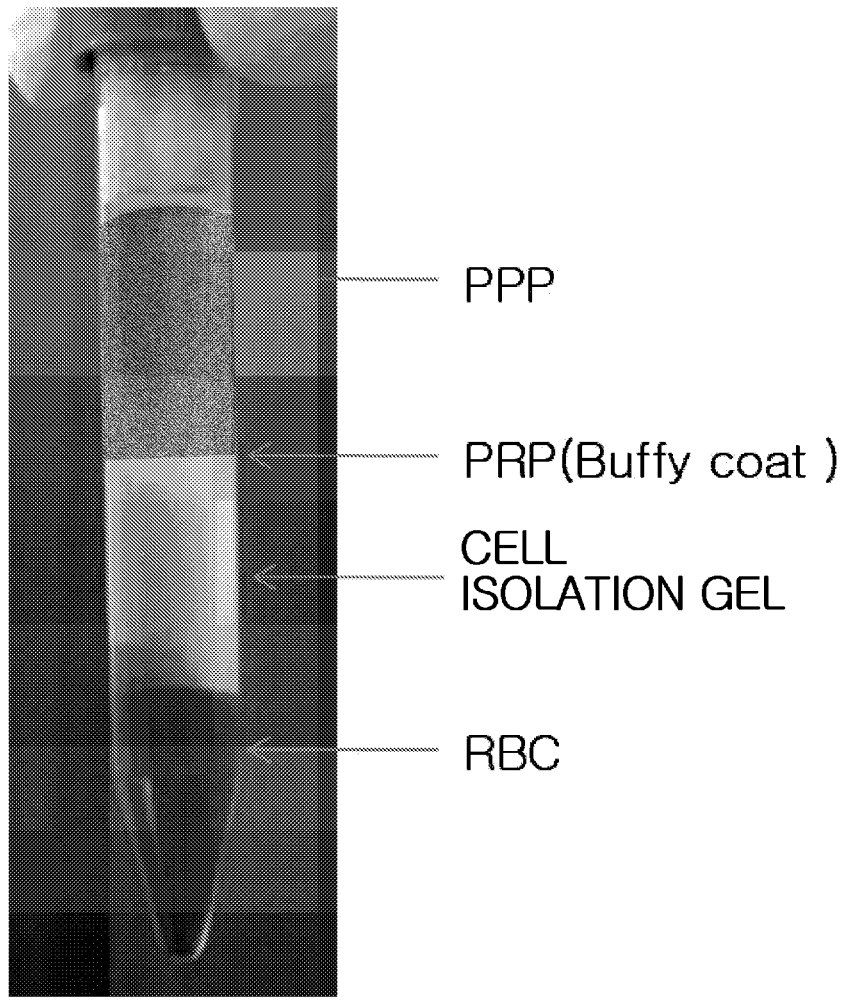
FIG. 2 shows that a whole blood is centrifugally separated to a conventional centrifugal separation tube in which a cell isolation gel is received.
Figure 3:
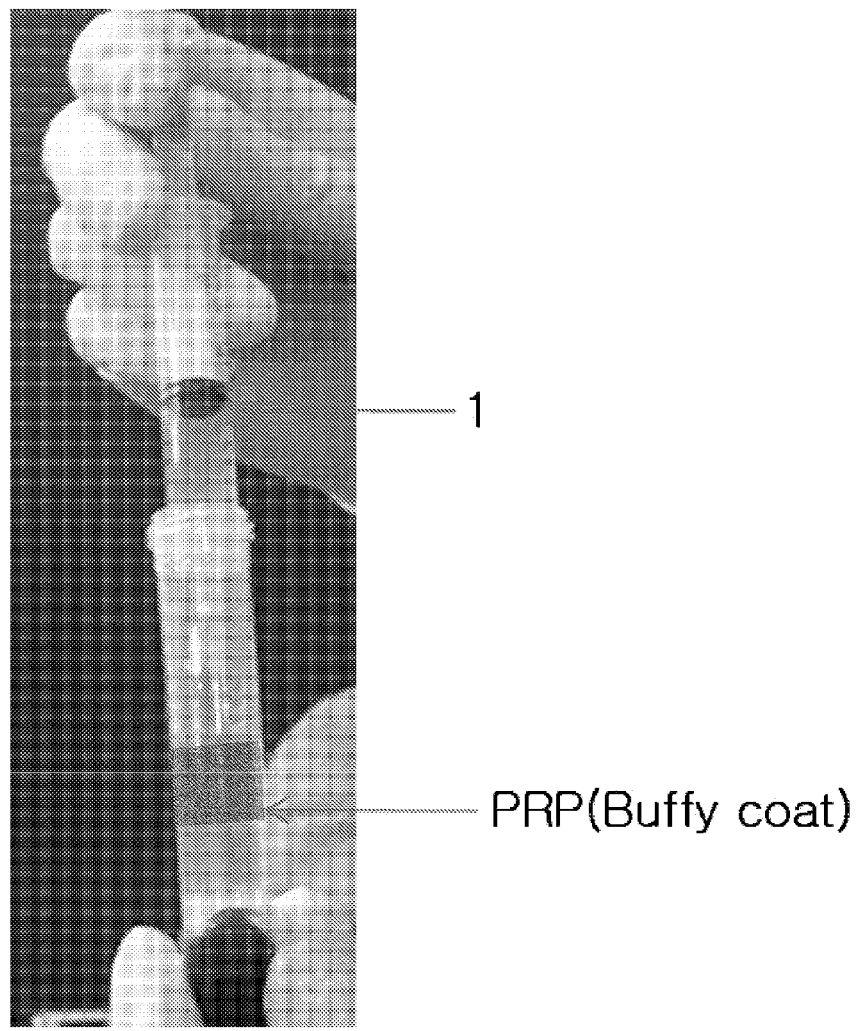
FIG. 3 shows that Platelet Rich Plasma (PRP) is extracted from the centrifugally separated blood of FIG. 2.
Figure 4:
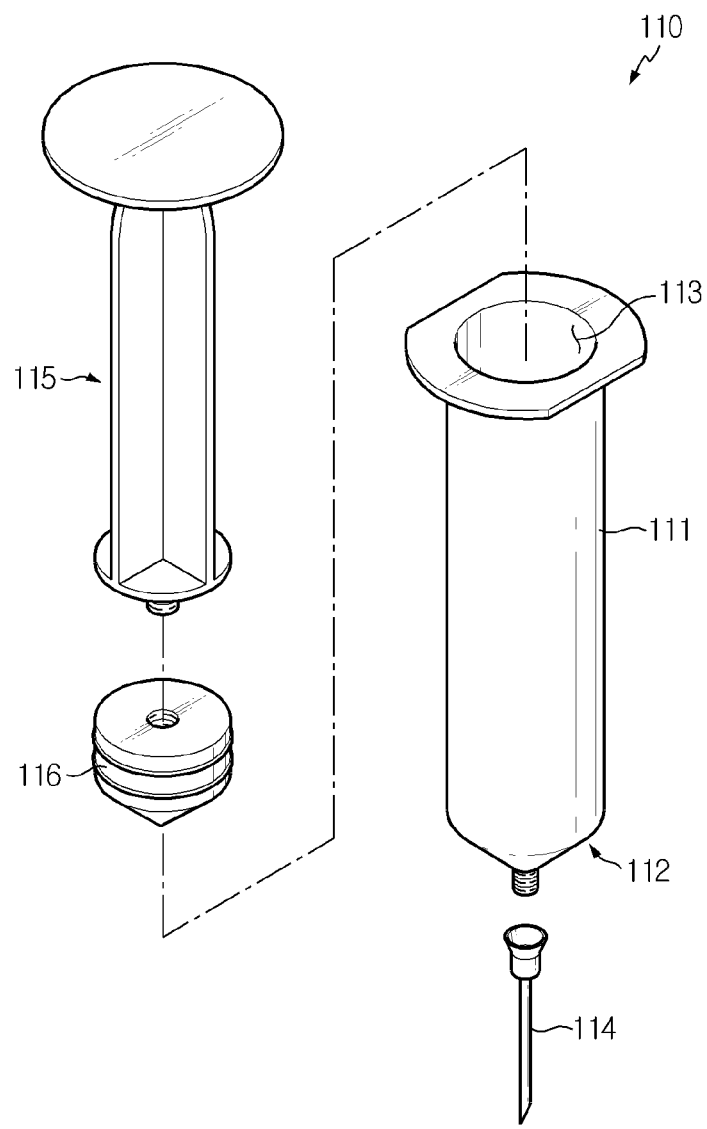
FIG. 4 is an exploded perspective view showing an injector provided to a centrifugal separation kit according to a preferred embodiment of the present disclosure.
Figure 5:
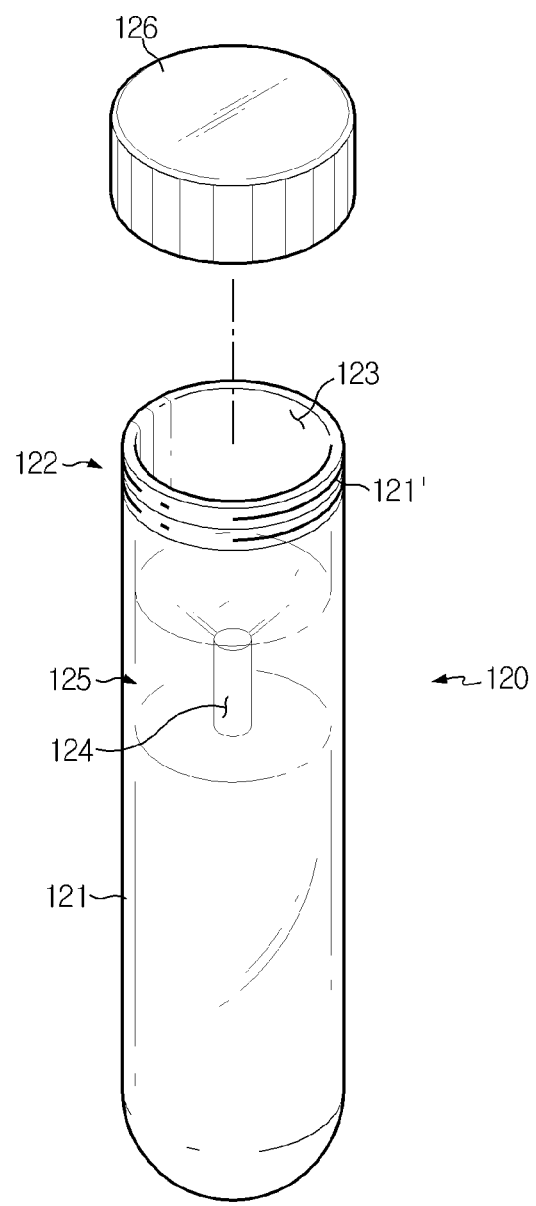
FIG. 5 is an exploded perspective view showing a centrifugal separation tube provided to the centrifugal separation kit according to a preferred embodiment of the present disclosure.

FIG. 4 is an exploded perspective view showing an injector provided to a centrifugal separation kit according to a preferred embodiment of the present disclosure, and FIG. 5 is an exploded perspective view showing a centrifugal separation tube provided to the centrifugal separation kit according to a preferred embodiment of the present disclosure.

Referring to FIGS. 4 and 5, the centrifugal separation kit 100 (see FIG. 8) includes an injector 110 and a centrifugal separation tube 120 to which the injector 110 may be installed.

The injector 110 includes a cylinder 111 having a lower portion to which an insert portion 112 is formed and an upper portion in which an opening 113 is formed, a piston 115 inserted from the open upper portion of the cylinder 111 and movable in a length direction of the cylinder 111, and an injection needle 114 installed to the lower portion of the cylinder 111.

The injector 110 as described above is a common one and is configured to collect blood in the cylinder 111. At this time, a rubber packing 116 installed to the piston 115 may be separated from the piston 115. In other words, when separating the rubber packing 116 from the piston 115, the piston 115 is removed while the rubber packing 116 is present in the injector 110.

Figure 6:
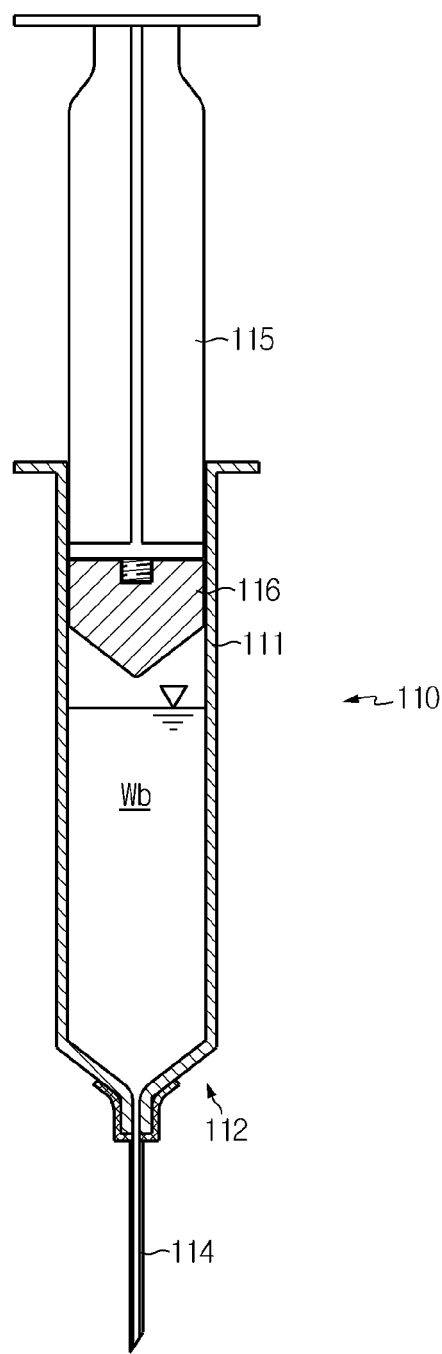
FIG. 6 is a cross-sectional view showing that blood is collected by using the injector of FIG. 4.

By using the injector 110, the whole blood Wb is collected (see FIG. 6).

The centrifugal separation tube 120 includes a tube body 121 having an upper portion where an open portion 123 is formed to receive a predetermined substance, a collecting unit 125 provided in the tube body 121, and a cap 126 for opening or closing the upper portion.

The tube body 121 is preferably made of transparent material, and a thread 121' is formed at the upper portion for coupling with the cap 126 and is screwed with the cap 126. At this time, the upper portion coupled with the cap 126, namely an upper portion based on the collecting unit 125, is a support 122. The support 122 plays a role of supporting the injector 122 when the injector 110 is inserted into the centrifugal separation tube 120. The support 122 will be described later.

At the center portion of the collecting unit 125, a collecting tube 124 communicating upper and lower sides based on the collecting unit 125 is formed. The collecting tube 124 is shaped and sized corresponding to the insert portion 112 of the injector 110. In other words, the upper portion of the collecting unit 125 is preferably shaped corresponding to a contacting surface of the injector 110 so that the insert portion 112 of the injector 110 is placed thereon and resultantly the injector 110 is closely adhered to the centrifugal separation tube 120. Accordingly, when the injector 110 is placed on the collecting unit 125, the insert portion 112 of the injector 110 is inserted into the collecting tube 124. Here, the collecting tube 124 preferably has a length greater than the length of the insert portion 112 of the injector. The collecting tube 124 may easily collect target substances and allow precise collection.

Meanwhile, the centrifugal separation tube 120 has an inner diameter equal to or greater than the injector 110, namely the outer diameter of the cylinder 111. For example, the inner diameter of the centrifugal separation tube 120 is set so that the outer circumference of the injector 110 is closely adhered to the inner circumference of the centrifugal separation tube 120.

Figure 7:
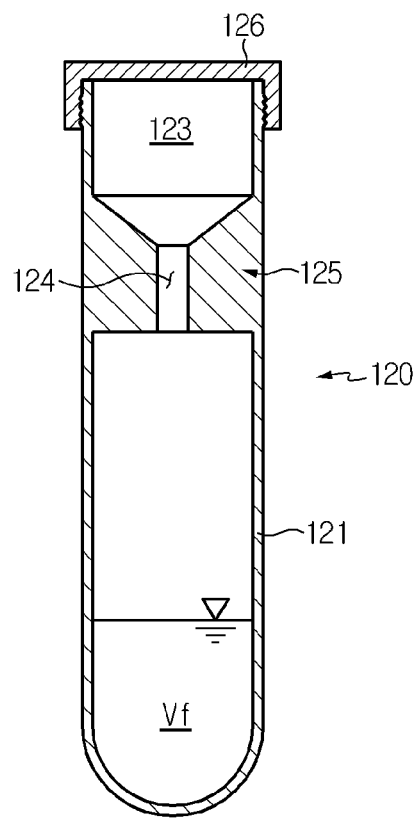
FIG. 7 is a cross-sectional view showing that the centrifugal separation tube of FIG. 5 is filled with the cell isolation gel.
Figure 11:
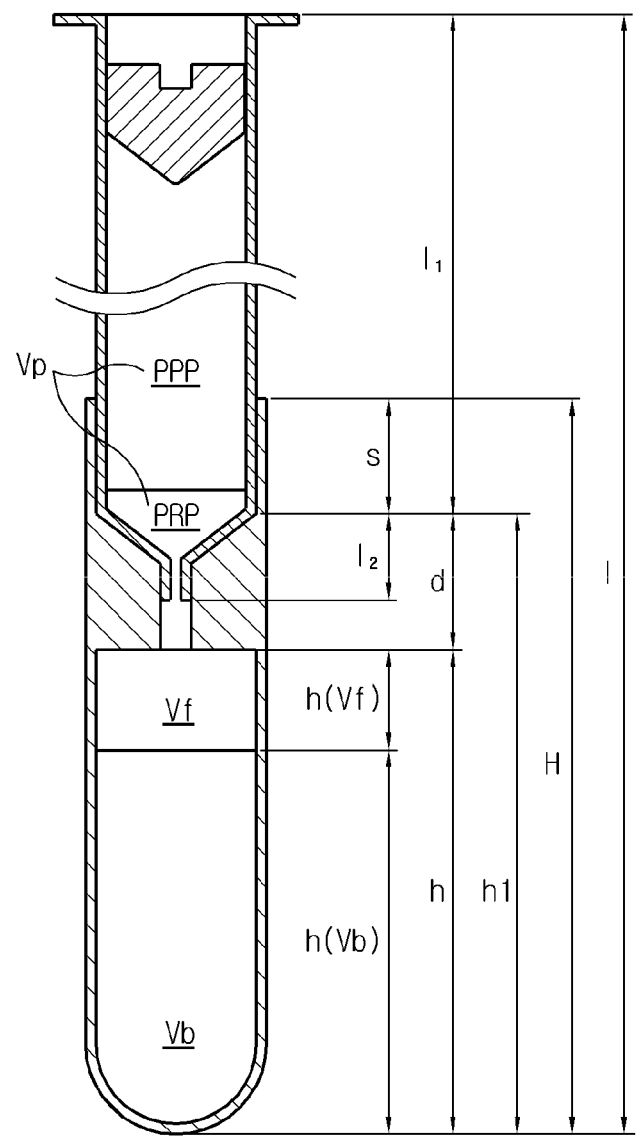
FIG. 11 is a cross-sectional view showing a centrifugally separated state by using the centrifugal separation kit according to the preferred embodiment of the present disclosure.

The centrifugal separation tube 120 as described above may be filled with a cell isolation gel Vf (see FIG. 7). The cell isolation gel Vf is used for separating the whole blood Wb into blood cell components Vb and blood plasma components Vp at the centrifugal separation, as shown in FIG. 11. The cell isolation gel Vf may be mixed with the whole blood Wb up to a maximum volume ratio of 1:1 depending on a target substance collector or may not be used at all depending on the situation.

In the embodiment of the present disclosure, it is assumed that the cell isolation gel Vf is used when the whole blood Wb is centrifugally separated.

Meanwhile, in the present disclosure, blood plasma components Vp are collected to the injector 110 installed to the collecting unit 125 during the centrifugal separation. Accordingly, it is important to set an installation location of the collecting unit 125 to the centrifugal separation tube 120. An embodiment for setting a location of the collecting unit 125 and a method for centrifugal separation will be described below.

Figure 8:
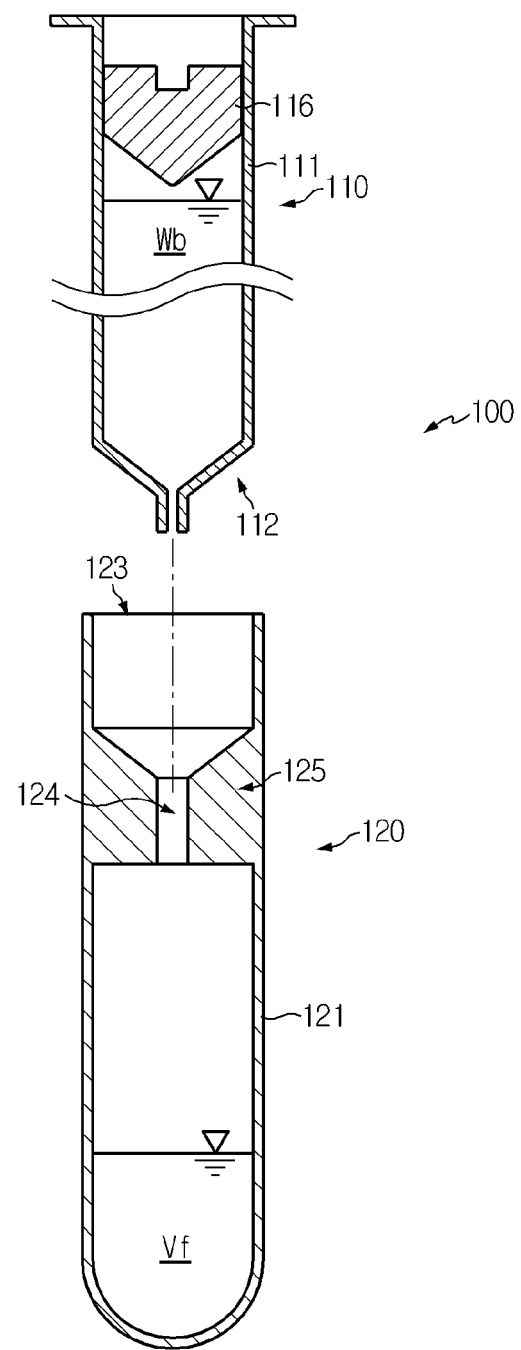
FIG. 8 is an exploded sectional view showing a centrifugal separation kit according to a preferred embodiment of the present disclosure.
Figure 9:
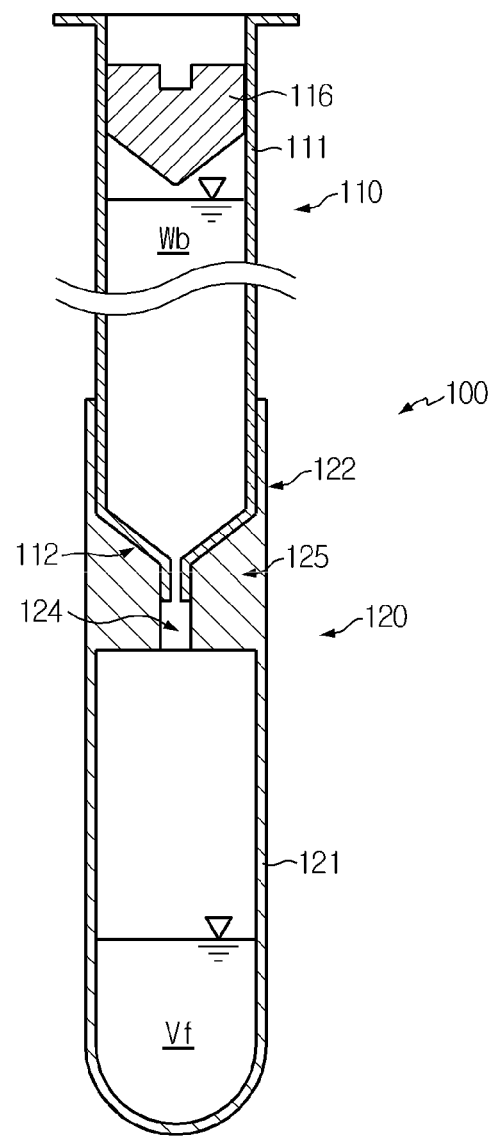
FIG. 9 is a cross-sectional view showing the centrifugal separation kit in an assembled state.
Figure 10:
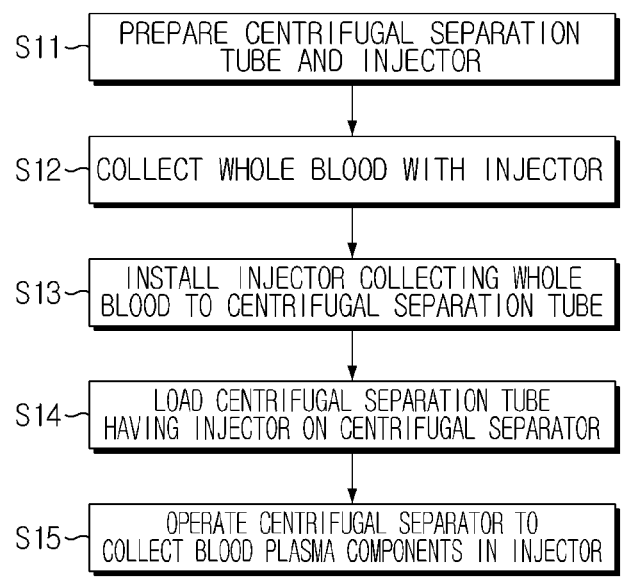
FIG. 10 is a flowchart for illustrating a method for centrifugal separation using the centrifugal separation kit according to a preferred embodiment of the present disclosure.

FIG. 8 is an exploded sectional view showing a centrifugal separation kit according to a preferred embodiment of the present disclosure, FIG. 9 is a cross-sectional view showing the centrifugal separation kit in an assembled state, and FIG. 10 is a flowchart for illustrating a method for centrifugal separation using the centrifugal separation kit according to a preferred embodiment of the present disclosure;

Referring to FIGS. 8 to 10, first, the centrifugal separation tube 120 and the injector 110 are prepared (S11). At this time, as shown in FIG. 7, the centrifugal separation tube 120 is filled with the cell isolation gel Vf.

Next, as shown in FIG. 6, the whole blood Wb is collected by using the injector 110 (S12).

Subsequently, the injector collecting the whole blood Wb is installed to the centrifugal separation tube 120 (S13). At this time, as shown in FIGS. 8 and 9, the injector needle 114 and the piston 115 are already removed from the injector 110. Here, when the piston 115 is removed, the piston 115 should be removed so that the rubber packing 116 is present. Depending on the situation, a separate rubber packing (not shown) may be used for packing the upper portion of the injector 110. The injector 110 from which the needle injector 114 and the piston 115 are removed is inserted through and installed to the open upper portion of the centrifugal separation tube 120 from which the cap 126 is removed. Here, the injection needle 114 is removed in order to easily facilitate the installation of the injector 110 to the centrifugal separation tube 120, and the piston 115 is removed except for the rubber packing 116 so that the centrifugal separation kit 100 may be easily loaded on a centrifugal separator (not shown) later.

The injector 110 is tightly installed by the support 122 formed at the upper portion of the centrifugal separation tube 120. In other words, the outer circumference of the injector 110 is closely adhered to the inner circumference of the centrifugal separation tube 120, and the injector 110 is supported as much as the length of the support 122. Here, the insert portion 112 of the injector 110 is inserted into the collecting tube 124.

Subsequently, the centrifugal separation tube 120 to which the injector 110 is installed is loaded on the centrifugal separator (S14).

After that, as shown in FIG. 11, the centrifugal separator is operated to separate the whole blood Wb into blood cell components Vb and blood plasma components Vp (S15). By the centrifugal separation, material with a high specific weight is located at a lower position, and material with a low specific weight is located at a high position. In other words, based on the lower end of the collecting unit 125, blood cell components Vb are formed at a lower side, and blood plasma components Vp are formed at an upper side. It is because the collecting unit 125 is located so that a space corresponding to the sum volume of the Red Blood Cell (RBC) Vb in the centrifugally separated whole blood Wb and the cell isolation gel Vf is formed in a lower portion thereof.

If the blood plasma components Vp are collected to the injector 110 together with the centrifugal separation through the above procedure, the blood plasma components Vp may be used instantly. Therefore, the working time taken for surgical procedures and bioengineering utilization using the blood plasma components Vp reduces, which improves the working efficiency. In addition, since it is not necessary to use a separate injector for extracting blood plasma components Vp, the waste of consumables may be prevented.

Figure 12:
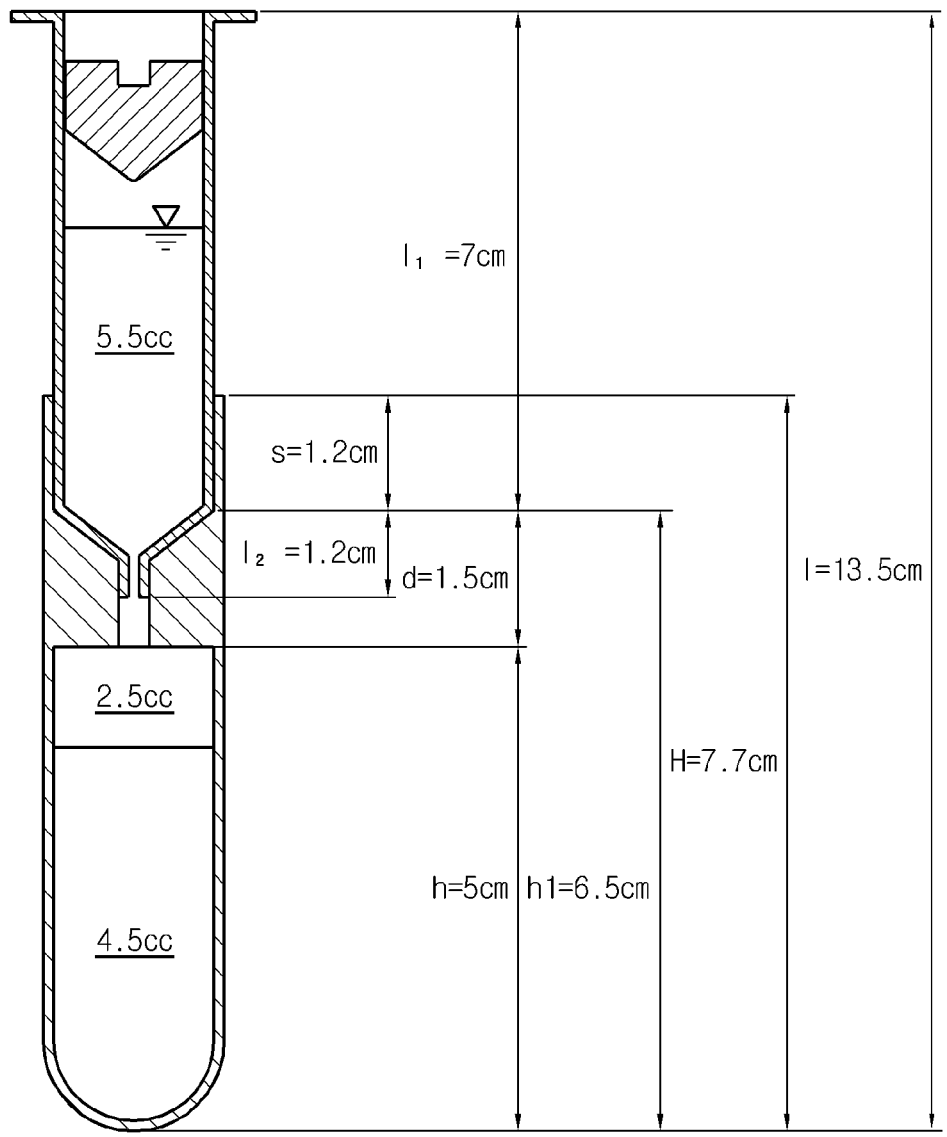
FIG. 12 shows given numerals of the centrifugal separation kit of FIG. 11 in a centrifugally separated state, according to the assumption of the present disclosure.

FIG. 11 is a cross-sectional view showing a centrifugally separated state according to the method of FIG. 10, and FIG. 12 shows given numerals of the centrifugal separation kit of FIG. 11 in a centrifugally separated state, according to the assumption of the present disclosure. Referring to FIGS. 11 and 12, a process of adjusting the location of the collecting unit will be described.

Hereinafter, restriction conditions of the use of the centrifugal separator, the injector and the centrifugal separation tube, and the volume of materials considered and used and the height according to the volume will be set in more detail.

The heights of the centrifugal separation tube and the injector are generally determined in consideration of the height at which they may be loaded on the centrifugal separator (not shown). For example, since a conventional centrifugal separation tube with a volume of 10 cc generally has a length of 13 cm, and since it may be mounted with a maximum length of 14 cm, the heights of the centrifugal separation tube and the injector are determined in this consideration.

Accordingly, the embodiment of the present disclosure proposes, as an example, a centrifugal separation tube and an injector which may be used for a centrifugal separator to which an article with a length of 14 cm may be loaded. The centrifugal separator has different length restrictions depending on its kind. Therefore, it is apparent to those having ordinary skill in the art that the design conditions of the centrifugal separation tube and the injector according to the present disclosure may be suitably selected depending on the kind of the centrifugal separator.

In the embodiment of the present disclosure, the injector 110 will be described with a 10 cc injector generally used as an example. The injector 110 is filled with 1.5 cc of ACD solution serving as an anticoagulant to prevent the blood from coagulating, and then the injector 100 collects 8.5 cc of the blood of a patient therein and is mounted to the centrifugal separation tube 120.

The cell isolation gel Vf is used for the centrifugal separation tube 120 in order to exclude the Red Blood Cell (RBC) and to accurately obtain the PRP (Platelet Rich Plasma). The cell isolation gel Vf may be mixed with the whole blood Wb at a maximum ratio of 1:1 or may not be used at all. Here, the cell isolation gel Vf is set to have a volume of 2.5 cc and a length of 2 cm. In other words, if 2.5 cc of cell isolation gel Vf is filled in the centrifugal separation tube 120, the cell isolation gel Vf has a height of 2 cm.

Meanwhile, when the whole blood Wb is centrifugally separated, the blood plasma component is represented by Vp and the blood cell component is represented by Vb. Here, since the specific weight of the blood cell components Vb is greater than the specific weight of the blood plasma components Vp, during the centrifugal separation, the blood cell components Vb are collected in a lower side.

Generally, when the whole blood Wb is centrifugally separated, the blood cell components, namely the Red Blood Cell (RBC) Vb has a volume ratio α of about 45% though it depends on a person whose blood is collected. Therefore, the volume Vb of the Red Blood Cell (RBC) with respect to the whole blood Wb 10 cc has a volumetric capacity of 4.5 cc, and is collected in a lower side of the centrifugal separation tube 120 within the height of 3 cm.

In other words, it could be understood that Wb=Vp+Vb, and 10 cc=5.5 cc+4.5 cc. In addition, since the sum of the volume of cell isolation gel Vf, which is 2.5 cc, and the volume Vb of the Red Blood Cell (RBC), which is 4.5 cc, is 7 cc, it could be found that the buffy coat, namely the PRP layer, is formed at the volumetric height of 7 cc. In other words, the blood plasma components Vp is formed in an upper side of the volumetric height of 7 cc.

Therefore, in the case where the centrifugal separation tube 120 is prepared in a normal way, if the cell isolation gel has a volumetric height of 2 cm and the blood cell volume has a volumetric height of 3 cm, the height h at which the collecting unit 125 is installed becomes 5 cm. In other words, the lower side of the collecting unit 125 should be located at a height of 5 cm.

From the above, the following equation 1 may be obtained.

$$A=(\alpha \times Wb)+Vf=Vb+Vf \quad \text{Equation 1}$$

where $0 \leq Vf \leq Wb$;
A is the sum of volumes of the blood cell components and the cell isolation gel;
Wb is a volume of the whole blood;
Vb is a volume of the Red Blood Cell (RBC);
α is a volume ratio of the centrifugally separated Red Blood Cell (RBC); and
Vf is a volume of the cell isolation gel.

As in Equation 1, it could be understood that the volumetric capacity of the lower space where the collecting unit 125 is formed is a volumetric capacity obtained by adding the volumes of the blood cell components Vb and the cell isolation gel Vf. In other words, the location of the lower side of the collecting unit 125 is preferably adjusted so that the volumetric capacity of A is received in the lower side of the collecting unit 125.

In addition, by using Equation 1, assuming that the height at which the collecting unit 125 is installed is h, that the volumetric height of the Red Blood Cell (RBC) Vb is h Vb, and that the volumetric height of the cell isolation gel Vf is h Vf, the following equation may be obtained.

$$h=h(Vf)+h(Vb) \quad \text{Equation 2}$$

where h is a height at which the collecting unit is installed.
In other words, the height h at which the collecting unit 125 is installed is h Vf+0.45×h Wb. Therefore, the height of the collecting unit 125 may be set based on Equation 2.

Meanwhile, assuming that the length of the collecting unit 125 is d and that the uppermost height of the collecting unit 125 where the injector 110 is installed is h1, h1=h+d, which will be the height at which the injector is mounted.

In addition, it is assumed that the length of the mounted injector 110 is $l_1$, and that the total length in which the injector 110 is mounted to the centrifugal separation tube 120, namely the length of the kit 100, is l. At this time, if the length d of the collecting unit 125 is set to be 1.5 cm in consideration of the height and special range mountable to the centrifugal separator and if $l_1$ is set to be 7 cm, the total length of the kit 100 becomes l=$l_1$+d+h. In other words, the total length l of the kit 100 is 13.5 cm. Therefore, the kit 100 has a length smaller than 14 cm which is the maximum length installable to the centrifugal separator, and therefore the kit 100 may be installed to the centrifugal separator.

In addition, it is assumed that the support 122 of the centrifugal separation tube 120 supporting the injector 110 is s, and that the length of the insert portion 112 of the injector 110 is $l_2$.

Here, assuming that the length of the centrifugal separation tube 120 is H, H=h+d+s=h1+s.

The support s is used for supporting the injector 110 and is preferably 1 cm to 2 cm. It is apparent that the length of the support s is not included in the total length l.

The length d of the collecting unit 125 is greater than the length $l_2$ of the insert portion 112. Here, if the length $l_2$ of the insert portion 112 is set to be 1.2 cm, $l_2$=1.2 cm<d.

In addition, due to the difference between the length d of the collecting tube 124 of the collecting unit 125 and the length $l_2$ of the insert portion 112 of the injector 110, a remainder space is present in the collecting tube 124. The blood plasma components Vp may be collected to the collecting tube 124 and the injector 110 together with the remainder space. As an alternative, by adjusting the volume of the cell isolation gel Vf, the blood plasma components Vp may be collected from the insert portion 112 of the injector 110. This may be implemented by further using the cell isolation gel Vf of a volume identical to the remainder space.

Meanwhile, the numerals depicted in FIG. 12 are arbitrary numerals determined by the assumption of the present disclosure, and it is apparent that the numerals may be changed depending on the kind and volumes of the injector and the centrifugal separation tube used.

As a result, by setting the location where the collecting unit 125 is installed according to the set conditions and equations as above, blood plasma components Vp may be collected to the injector 110. Therefore, since desired blood plasma components Vp are collected in the injector 110, they may be instantly used secondarily, and the waiting time of a person who performs or receives a surgery decreases, thereby improving the working efficiency.

Figure 13:
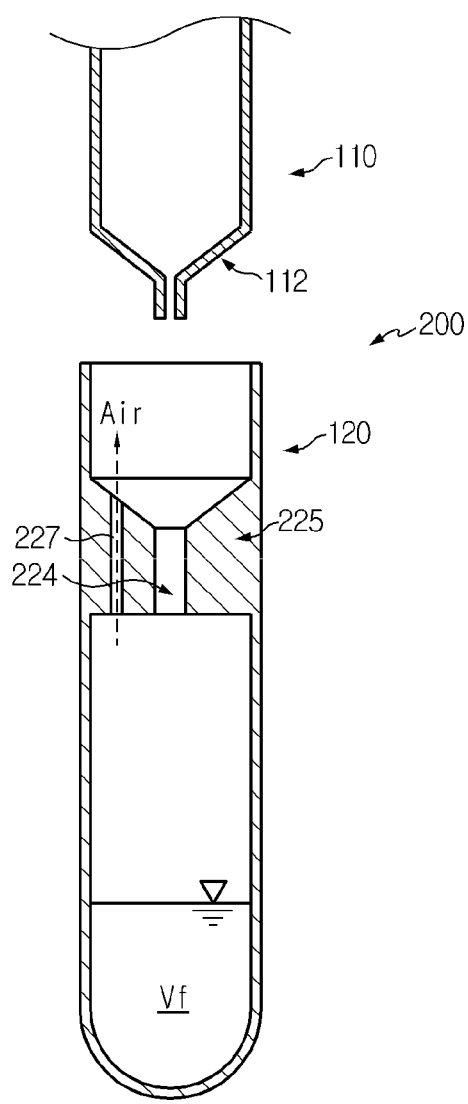
FIG. 13 is a cross-sectional view showing another centrifugal separation tube provided to the centrifugal separation kit according to the preferred embodiment of the present disclosure.
Figure 14:
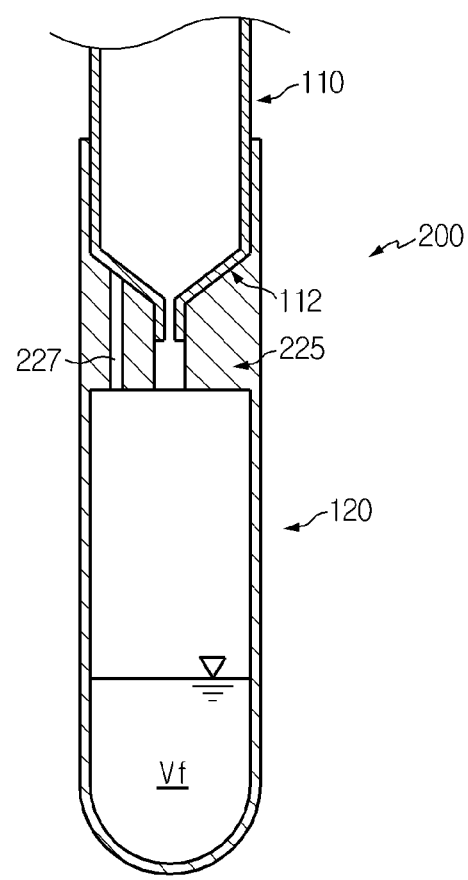
FIG. 14 is a cross-sectional view showing that an injector is installed to the centrifugal separation tube of FIG. 13.

FIG. 13 is a cross-sectional view showing another centrifugal separation tube provided to the centrifugal separation kit according to the preferred embodiment of the present disclosure, and FIG. 14 is a cross-sectional view showing that an injector is installed to the centrifugal separation tube of FIG. 13.

Referring to FIGS. 13 and 14, a centrifugal separation kit 200 includes an injector 110 and a centrifugal separation tube 120 in which a collecting unit 225 with a ventilation hole 227 is formed. At this time, among the components of the centrifugal separation kit 200, the injector 110 is identical to the injector 110 shown in FIG. 9 and is not described in detail here. In addition, any reference numeral of FIGS. 13 and 14 identical to that of FIG. 9 designates the same component as in FIG. 9. In other words, this embodiment is substantially identical to the former embodiment, except that the ventilation hole 227 is formed in the collecting unit 225.

The ventilation hole 227 is formed in the collecting unit 225. The ventilation hole 227 is formed for easy installation of the injector 110 to the centrifugal separation tube 120. In other words, as the whole blood drops from the injector 110, the air in the centrifugal separation tube 120 discharges out, thereby allowing the whole blood Wb to easily drop. The ventilation hole 227 is closed as the injector 110 is closely adhered to and placed on the upper portion of the collecting unit 225, so that the whole blood Wb does not escape through the ventilation hole 227.

Meanwhile, as an alternative of the ventilation hole 227, a hole (not shown) may be formed in the injector 110. In other words, as the hole is formed in the upper side of the injector 110, the whole blood Wb may easily flow into the centrifugal separation tube 120.

The collecting unit 225 with the ventilation hole 227 may be provided at a previously designated location, so that the blood plasma components Vp may be collected in the injector 110 by means of the method for centrifugal separation described above, as apparent to those having ordinary skill in the art.

Meanwhile, even though it has been illustrated and described that the heights of the collecting units 125 and 225 are determined by the setting conditions, the heights of the collecting units 125 and 225 may be adjusted, without being limited thereto.

Figure 15:
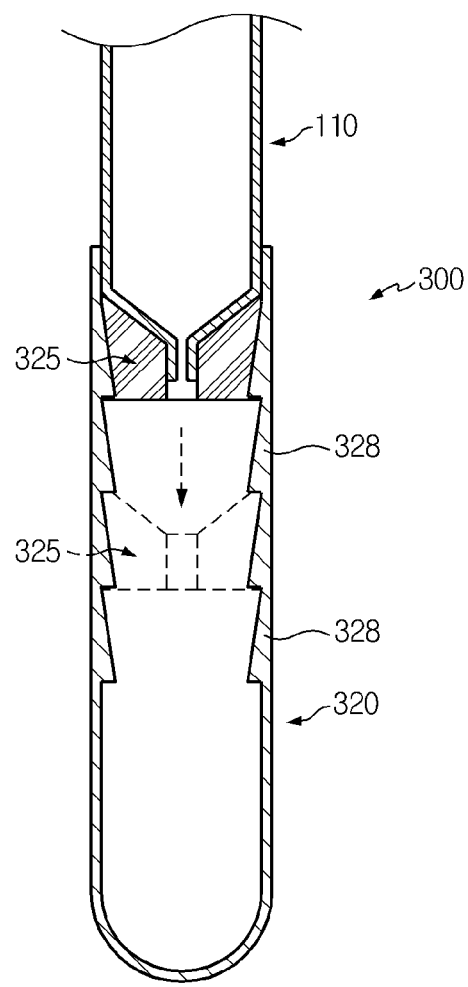
FIG. 15 is a cross-sectional view showing another centrifugal separation tube provided to the centrifugal separation kit according to the preferred embodiment of the present disclosure.

For example, as shown in FIG. 15, protrusions 328 are formed in a centrifugal separation tube 320. At this time, the centrifugal separation kit 300 shown in FIG. 15 is another embodiment having a modified centrifugal separation tube 320, and the same reference numerals in FIG. 15 as in FIG. 9 designate the same components as in FIG. 9.

The protrusions 328 formed in the centrifugal separation tube 320 are formed with a slant at regular intervals in the length direction of the centrifugal separation tube 320. In other words, the collecting unit 325 is pressed by the injector 110 to move downwards as much as the interval of the protrusions 328. At this time, the collecting unit 325 having moved downwards is not moved upwards. Therefore, when the injector 110 is pulled in a discharging direction, the Platelet Rich Plasma (PRP) collected in the insert portion 112 of the injector 110 coupled with the collecting tube 324 is not mixed with another layer due to the movement of the collecting unit 325 but is maintained tranquilly.

Figure 16:
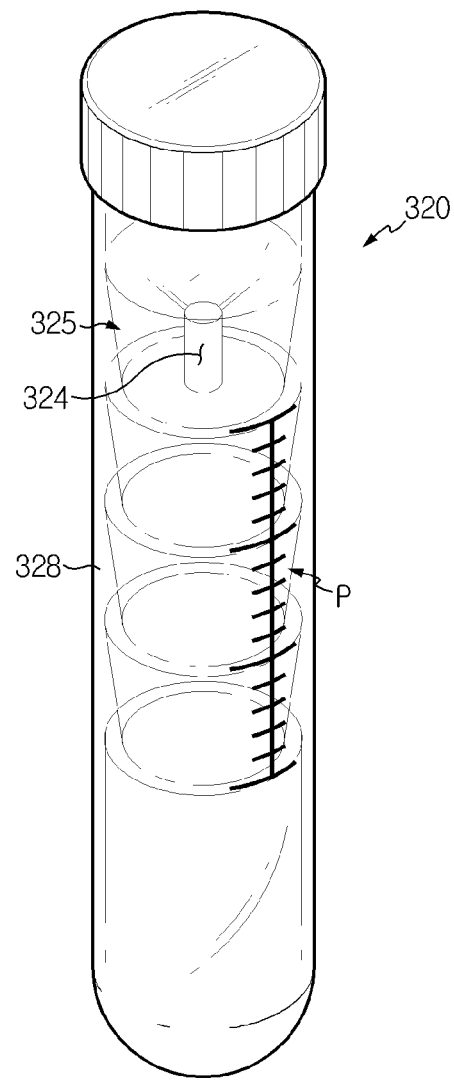
FIG. 16 is a perspective view showing the centrifugal separation tube of FIG. 15.

In more detail, the centrifugal separation tube 320 having the protrusions 328 is made of transparent material, and gradations P are marked on the outer circumference thereof (see FIG. 16). The gradations p are marked to adjust a location according to the sum of the volume Vb of the Red Blood Cell (RBC) layer of the whole blood and the volume Vf of the filled cell isolation gel. In other words, the gradations p are marked at every interval of the protrusion 328 so that the location of the collecting unit 325 may be adjusted according to the sum of the volume Vb of the Red Blood Cell (RBC) and the volume Vf of the cell isolation gel.

For example, as described above, when 10 cc of the whole blood and 2.5 cc (2 cm) of the cell isolation gel are basically used, if 9 cc of the whole blood is collected so that the volume of the Red Blood Cell (RBC) becomes 4 cc and a resultant volumetric height is 2.5 cm, '9 (not shown)' is marked as the gradation p at a location distanced from the lower side of the tube by 4.5 cm. In other words, the gradation p marked as '9' means a corresponding height at which 9 cc of blood is collected. Therefore, a person who performs a surgery pushes and mounts the collecting unit 325 as much as the sum of volumes of the collected blood and the cell isolation gel, and then performs the method for centrifugal separation.

Figure 17:
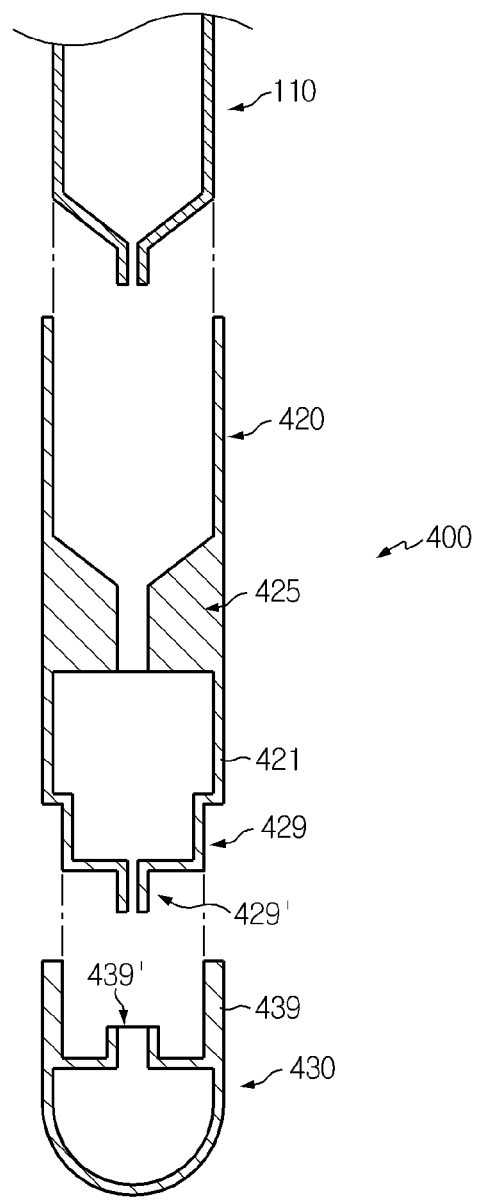
FIG. 17 is an exploded sectional view showing another centrifugal separation kit according to a preferred embodiment of the present disclosure.
Figure 18:
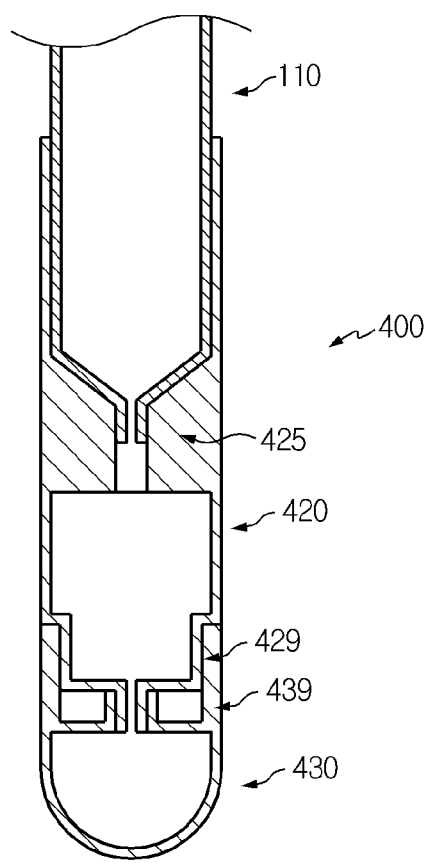
FIG. 18 is an assembled sectional view of FIG. 17.

FIG. 17 is an exploded sectional view showing another centrifugal separation kit according to a preferred embodiment of the present disclosure, and FIG. 18 is an assembled sectional view of FIG. 17.

Referring to FIGS. 17 and 18, the centrifugal separation kit 400 includes an injector 110, a centrifugal separation tube 420 to which the injector 110 may be installed, and a lower cap 430 installed to the lower side of the centrifugal separation tube 420. At this time, among the components of the centrifugal separation kit 400, the injector 110 is identical to the injector 110 shown in FIG. 9 and is not described in detail here. In addition, among reference numerals in FIGS. 17 and 18, the same reference numeral as in FIG. 9 designates the same component.

The centrifugal separation tube 420 includes a tube body 421 having an upper portion in which an opening is formed and a lower portion in which a tube insert portion 429' is formed, and a collecting unit 425 provided in the tube body 421.

The injector 110 is inserted through the open upper portion of the tube body 421 and is placed on the collecting unit 425. At this time, the injector 110 is tightly installed as the outer circumference of the injector 110 is closely adhered to the inner circumference of the tube body 421.

A coupling unit 429 having the tube insert portion 429' is provided to the lower portion of the tube body 421. The tube insert portion 429' is configured to communicate the inside and the outside of the tube body 421.

The lower cap 430 includes a fastening portion 439' protruding upwards to seal the tube insert portion 429', and a tube coupling portion 439 installed to the coupling unit 429. At this time, the lower cap 430 may be filled with a predetermined amount of cell isolation gel. At this time, the cell isolation gel may not be filled through the upper portion of the tube body 421, the tube insert hole 429' is sealed by the lower cap 430. In other words, by installing the lower cap 430 to the tube body 421, the centrifugal separation tube having a closed lower portion may be used.

Figure 19:
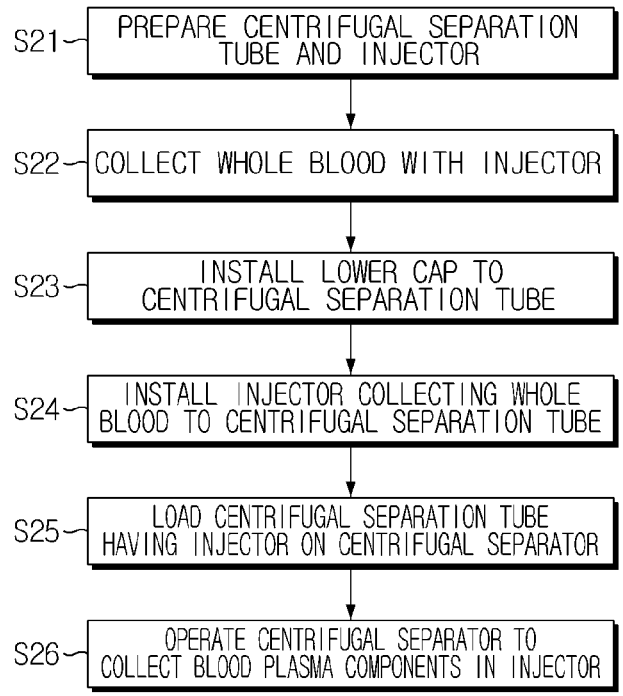
FIG. 19 is a flowchart for illustrating a method for centrifugal separation using another centrifugal separation kit according to the preferred embodiment of the present disclosure.

A method for centrifugal separation using the centrifugal separation kit 400 configured as above will be described with reference to FIG. 19.

The method for centrifugal separation according to the present disclosure is composed of six steps. In other words, the method may include preparing a centrifugal separation tube 420 and an injector 110 (S21), collecting the whole blood by using the injector 110 (S22), installing the lower cap 430 to the lower side of the centrifugal separation tube 420 (S23), installing the injector 110 collecting the whole blood to the centrifugal separation tube 420 (S24), loading the centrifugal separation tube 420 to which the injector 110 is installed on a centrifugal separator (not shown) (S25), and operating the centrifugal separator to collect blood plasma components into the injector (S26).

In this process, all steps except for the step S23 are identical to the steps S11 to S15 described above. In other words, the method for centrifugal separation including the step S23 may be easily understood from the former method for centrifugal separation and is therefore not described in detail here.

In relation to the step S23, the lower cap 430 is installed to the centrifugal separation tube 420. At this time, the lower cap 430 is filled with a predetermined amount of cell isolation gel. Here, the cell isolation gel is preferably filled by 2 cc to 2.5 cc.

The lower cap 430 is configured so that the variable height of Platelet Rich Plasma (PRP) may be adjusted. For example, if the Platelet Rich Plasma (PRP) is located at the lower side of the collecting unit 425, the lower cap 430 is more closely adhered and coupled to the tube body 421. In an opposite case, the lower cap 430 is coupled to but not closely adhered to the tube body 421.

Figure 20:
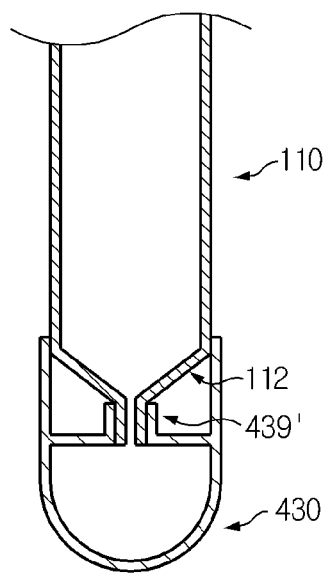
FIG. 20 is a cross-sectional view showing that a lower cap provided to another centrifugal separation kit according to the preferred embodiment of the present disclosure is installed to the injector.

Additionally, the lower cap 430 may be coupled to the injector 110 to seal the insert portion 112 of the injector 110. In other words, as shown in FIG. 20, the lower cap 430 is coupled to the injector 110. In other words, the insert portion 112 of the injector 110 is coupled to the fastening portion 439' of the lower cap 430, and the lower cap 430 is coupled to surround the lower portion of the injector.

The coupling between the lower cap 430 and the injector 110 is used for enriching the platelets secondarily. In other words, when the Platelet Rich Plasma (PRP) is secondarily enriched, the lower cap 430 is installed to the injector 110 in which Platelet Rich Plasma (PRP) is already extracted, thereby performing centrifugal separation. If the secondary centrifugal separation is performed, Platelet Rich Plasma (PRP) is accumulated in the lower cap 430, and PPP (Platelet Pure Plasma) is accumulated in the injector 110.

As a result, by using the centrifugal separation kit 100, 200, 300, 400 as above, blood plasma components may be easily and stably extracted. Meanwhile, the above embodiments may be used independently, or may be selectively combined and used, as apparent to those having ordinary skill in the art.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

INDUSTRIAL APPLICABILITY

The centrifugal separation kit and the method for centrifugal separation using the same according to the present disclosure give the following effects.

First, the centrifugal separation process and the collecting process for extracting Platelet Rich Plasma (PRP) from the blood or extracting stem cells from the bone marrow may be simplified, which reduces time taken for the work. Accordingly the waiting time of a person who performs or receives a surgery may be reduced.

Second, since a desired target substance may be stably collected in the injector, reliability and surgical safety may be ensured. In other words, since a separator injector for extracting a target substance is not used, it is possible to reduce the costs for consumables.

What is claimed is:
1. A centrifugal separation kit installed to a centrifugal separator to divide blood into blood cell components composed of a Red Blood Cell (RBC) layer and blood plasma components composed of a Platelet Rich Plasma (PRP) layer and a PPP (Platelet Poor Plasma) layer in order from a bottom thereof, comprising:
   a) an injector having an opening at an upper portion thereof so that a piston having a rubber packing installed thereto is movably inserted into the upper portion through the opening, the injector having a first predetermined volumetric capacity corresponding to a known volume of whole blood (Wb) and an insert portion at a lower portion thereof to which an injector needle is installed thereto; and
   b) a centrifugal separation tube loadable on the centrifugal separator with the injector installed thereto, comprising:
      a lower portion having a second predetermined volumetric capacity,
      a collecting unit having a collecting channel of an elongated shape at a center thereof, wherein the lower portion of the centrifugal separation tube is connected with a lower end of the collecting channel and the insert portion of the injector is frictionally engaged into an upper end of the collecting channel, thereby the collecting channel providing a direct fluid communication between the lower portion and an internal space of the injector while the blood is being centrifugally separated, wherein the centrifugal separation tube is configured for including a predetermined amount of cell isolation gel having a volume of equal or greater than 0, and wherein a lower side of the collecting unit has an adjusted location so that the second predetermined volumetric capacity is substantially equal to the sum of the volume of the cell isolation gel and a predetermined fraction of the first predetermined volumetric capacity, wherein the predetermined fraction corresponds to a known volume of RBCs (Vb) present in the known volume of whole blood (Wb).

2. The centrifugal separation kit according to claim 1, wherein the centrifugal separation tube has an inner diameter equal to or greater than an outer diameter of the injector, and wherein an outer surface of the injector is frictionally engaged to an inner surface of the centrifugal separation tube.

3. The centrifugal separation kit according to claim 1, wherein an upper portion of the collecting unit is shaped corresponding to a contact surface of the injector so that the insert portion of the injector is inserted into and frictionally engaged to the collecting channel and wherein the collecting channel has a length greater than a length of the injector insert portion.

4. The centrifugal separation kit according to claim 1, wherein the second predetermined volumetric capacity (A) of the lower portion of the centrifugal separation tube, a volume (Wb) of the blood corresponding to the first predetermined volumetric capacity, a volume (Vb) of the Red Blood Cell (RBC) layer, a volume ratio ($\alpha$) of the Red Blood Cell (RBC) layer based on the volume of (Wb) of the blood, and a volume (Vf) of the cell isolation gel satisfy the following relation:

$$A=(\alpha \times Wb)+Vf=Vb+Vf; \text{ and}$$

$$0 \leq Vf \leq Wb.$$

5. The centrifugal separation kit according to claim 1, wherein a ventilation hole is formed in the collecting unit, and wherein the ventilation hole is closed as the injector is installed and frictionally engaged to the collecting unit.

6. The centrifugal separation kit according to claim 1, wherein inclined protrusions are formed at regular intervals on an inner side of the centrifugal separation tube along a length direction of the centrifugal separation tube, and the collecting unit moves downwards as much as the interval of the protrusions due to a pressing force applied from the injector so as not to move upwards.

7. The centrifugal separation kit according to claim 6, wherein the centrifugal separation tube is made of transparent material, and gradations representing a volume of the space located in the interval of the protrusions are marked on an outer circumference of the centrifugal separation tube so that the location of the collecting unit is adjusted according to the sum of a volume of the Red Blood Cell (RBC) layer in the collected whole blood and a volume of the filled cell isolation gel.

* * * * *